US012758668B2

(12) United States Patent
Finnegan

(10) Patent No.: US 12,758,668 B2
(45) Date of Patent: Oct. 13, 2026

(54) SCENT DISPENSER AND AUTOMATIC DISPENSE OF SCENT IN AN IMMERSIVE ENVIRONMENT

(71) Applicant: Dean Finnegan, Pleasanton, CA (US)

(72) Inventor: Dean Finnegan, Pleasanton, CA (US)

(73) Assignee: ELEVATED PERCEPTIONS LLC, Oceanside, CA (US)

( * ) Notice: Subject to any disclaimer, the term of this patent is extended or adjusted under 35 U.S.C. 154(b) by 410 days.

(21) Appl. No.: 18/133,422

(22) Filed: Apr. 11, 2023

(65) Prior Publication Data

US 2024/0226359 A1 Jul. 11, 2024

Related U.S. Application Data

(60) Provisional application No. 63/343,472, filed on May 18, 2022.

(51) Int. Cl.
*A61L 9/03* (2006.01)

(52) U.S. Cl.
CPC ............... *A61L 9/035* (2013.01); *A61L 9/037* (2013.01); *A61L 2209/111* (2013.01)

(58) Field of Classification Search
CPC ..... A61L 9/035; A61L 9/037; A61L 2209/111
USPC .......................................................... 700/283
See application file for complete search history.

(56) References Cited

U.S. PATENT DOCUMENTS

2012/0000989 A1* 1/2012 Bordier .................. A61L 9/122 239/34
2023/0149819 A1* 5/2023 Pandhare ............. H04L 65/612 709/217

* cited by examiner

*Primary Examiner* — Michael J Brown
(74) *Attorney, Agent, or Firm* — Plager Schack LLP; Mark H. Plager; Alexis Saenz

(57) ABSTRACT

A device and system automatically release scents in an immersive environment. When an audio signal includes a sound associated with an event correlated to one of the scents, the device releases the scent to provide the improved immersive experience with the sense of smell included in the scene. The occurrence of an event may be predicted by an artificial intelligence engine. The artificial intelligence engine may determine when an event associated with a scent to be dispensed is going to occur so that the timing of the dispense is more accurate and correlated with the timing of the action in the audio signal.

20 Claims, 20 Drawing Sheets

SCENT DISPENSER AND AUTOMATIC DISPENSE OF SCENT IN AN IMMERSIVE ENVIRONMENT

CROSS-REFERENCE TO RELATED APPLICATIONS

This application claims benefit under 35 U.S.C. § 119(e) of U.S. Provisional Application having Ser. No. 63/343,472 filed May 18, 2022, which is hereby incorporated by reference herein in its entirety.

BACKGROUND

The embodiments herein relate generally to entertainment systems, and more particularly to, scent dispenser.

Many entertainment experiences provide only visual, audio, and sometimes tactile feedback to the user. There is a lack of providing olfaction to users that limits an immersive experience, whether it be in the consumption of movies, gaming, virtual reality or the like. One issue with other previous devices is a lack of automation. Some previous approaches to releasing a scent during a user experience involved a technician manually mass releasing a scent into an audience. There was a disconnect between the smell reaching the individual audience members and the current scene since the smell had a slow diffusion rate in a wide area. The manual aspect also made it difficult for the technician to properly time the dispense.

As can be seen, there is a need in the field for an automated dispensing of scents for an improved immersive experience.

SUMMARY

According to one embodiment of the subject technology, a method for automatically dispensing a scent into an environment is disclosed. The method includes continuously detecting by a sensor or a computer processor, an audio signal in the environment. Data points in the audio signal are forwarded to an artificial intelligence engine. The artificial intelligence engine identifies one or more precursors and patterns from the audio signal associated with an event. The artificial intelligence engine predicts an occurrence of the event based on the precursors and patterns identified in the audio signal. The prediction is forwarded to a computing device or a controller forwarding the prediction to a computing device or a controller communicatively coupled to a scent dispenser coupled to a scent dispenser. The computing device identifies a scent correlated to the event. The computing device or the controller operates a dispense of the identified scent by the scent dispenser into the environment in association with a predicted occurrence of the event.

In another embodiment, a computer program product for automatically dispensing a scent into an environment is disclosed. The computer program product comprises one or more computer readable storage media, and program instructions collectively stored on the one or more computer readable storage media. The program instructions include continuously detecting by a sensor or a computer processor, an audio signal in the environment. Data points in the audio signal are forwarded to an artificial intelligence engine. The artificial intelligence engine identifies one or more precursors and patterns from the audio signal associated with an event. The artificial intelligence engine predicts an occurrence of the event based on the precursors and patterns identified in the audio signal. The prediction is forwarded to a computing device or a controller forwarding the prediction to a computing device or a controller communicatively coupled to a scent dispenser coupled to a scent dispenser. The computing device identifies a scent correlated to the event. The computing device or the controller operates a dispense of the identified scent by the scent dispenser into the environment in association with a predicted occurrence of the event.

BRIEF DESCRIPTION OF THE FIGURES

The detailed description of some embodiments of the present invention is made below with reference to the accompanying figures, wherein like numerals represent corresponding parts of the figures.

DETAILED DESCRIPTION OF CERTAIN EMBODIMENTS

Figure 1:
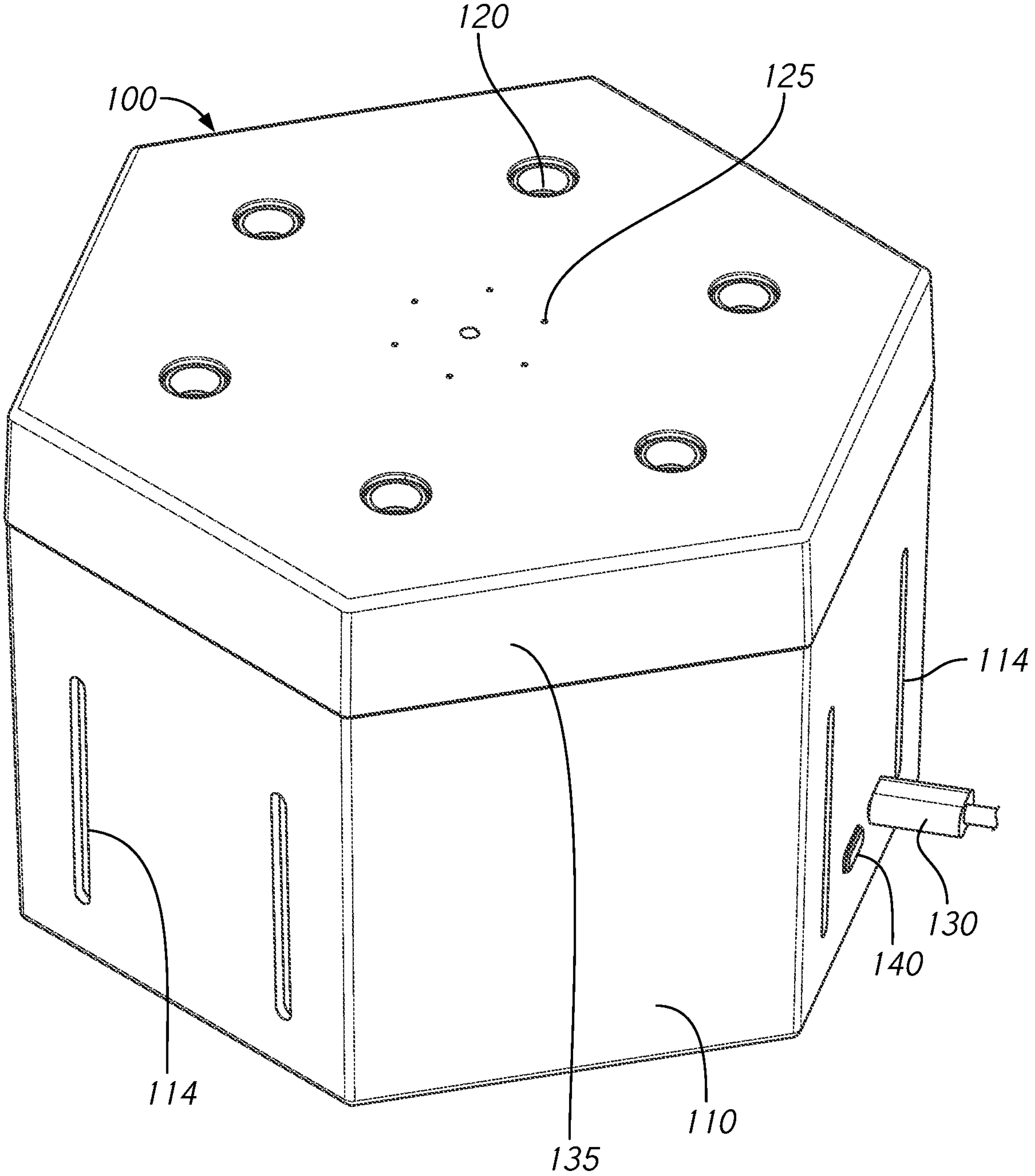
FIG. 1 is a front perspective view of an automated scent dispenser for an immersive experience in accordance with an illustrative embodiment of the subject technology.
Figure 2:
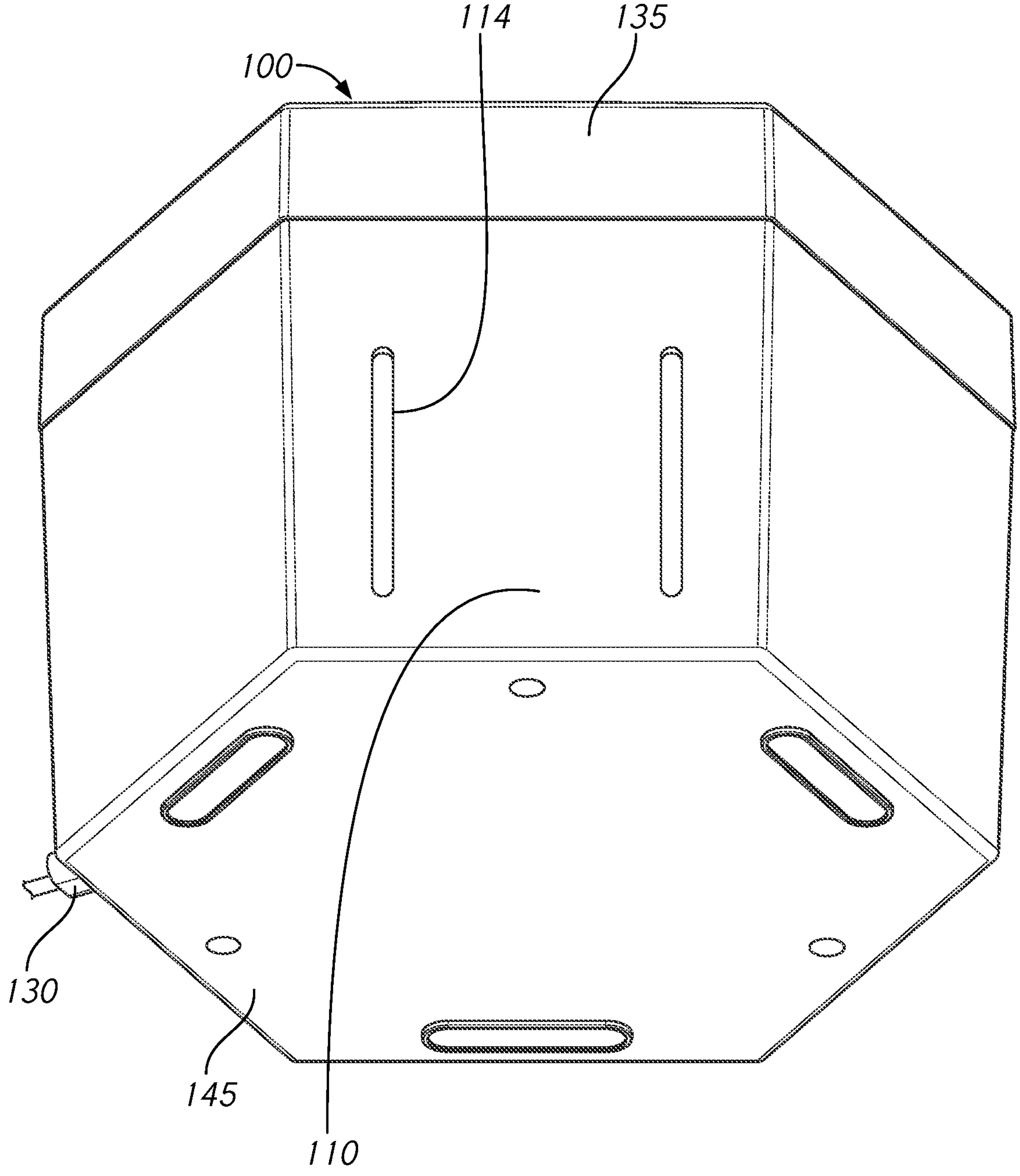
FIG. 2 is a bottom perspective view of the dispenser of FIG. 1.
Figure 3:
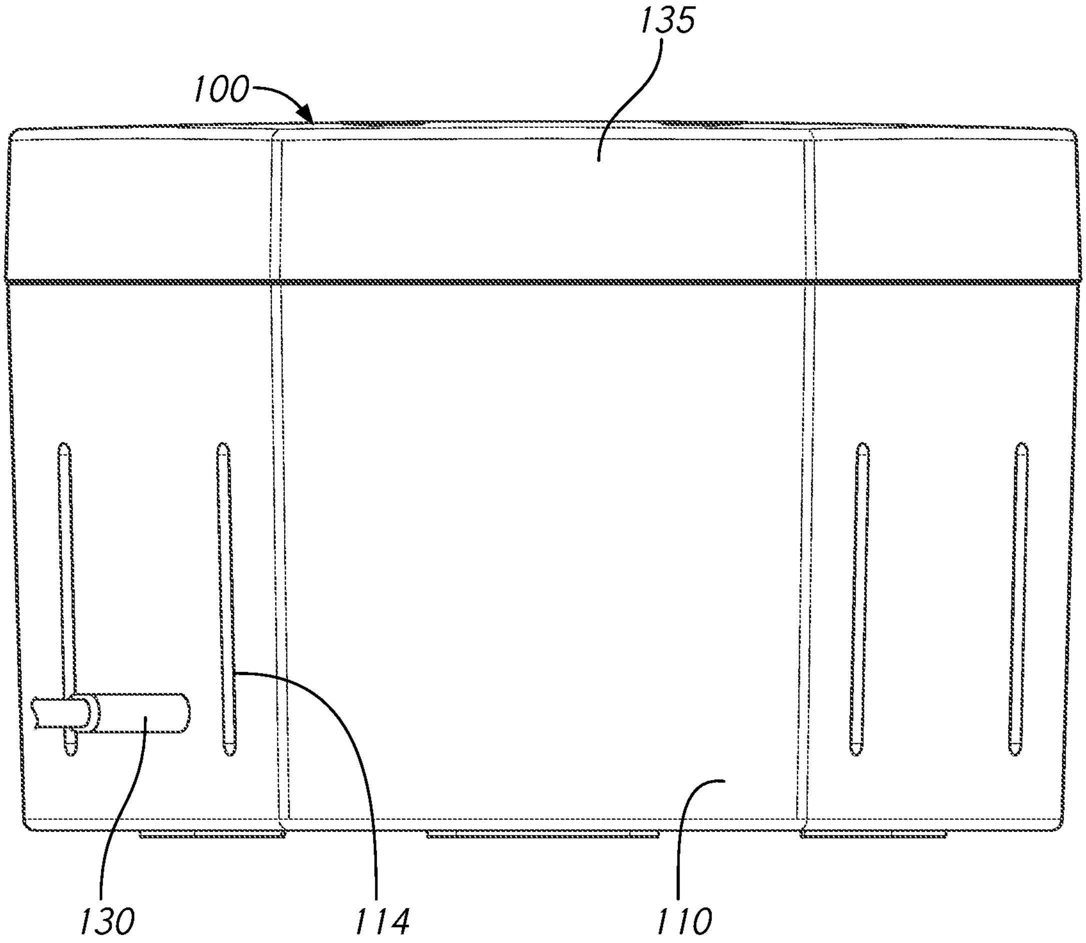
FIG. 3 is a rotated side view of the dispenser of FIG. 1.
Figure 4:
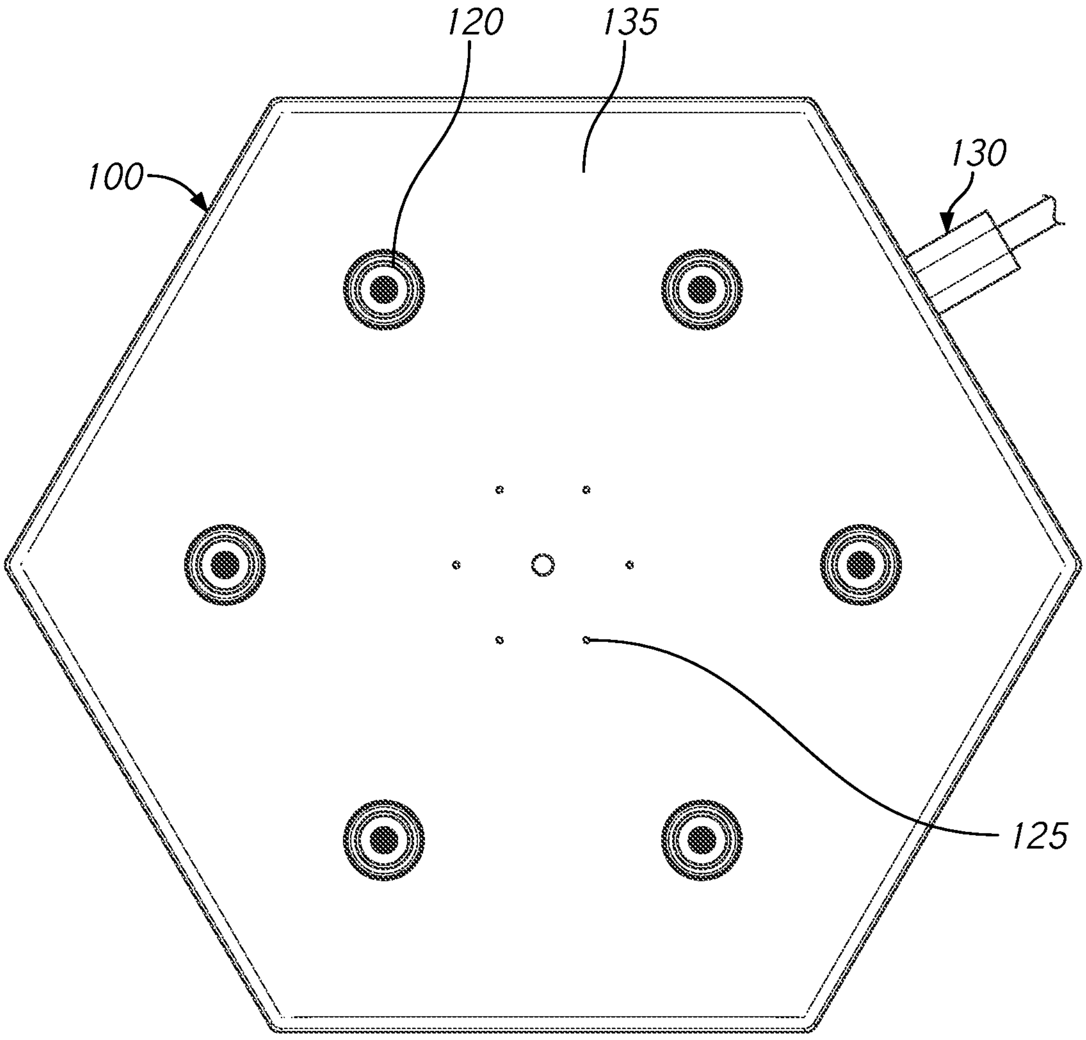
FIG. 4 is a top view of the dispenser of FIG. 1.
Figure 5:
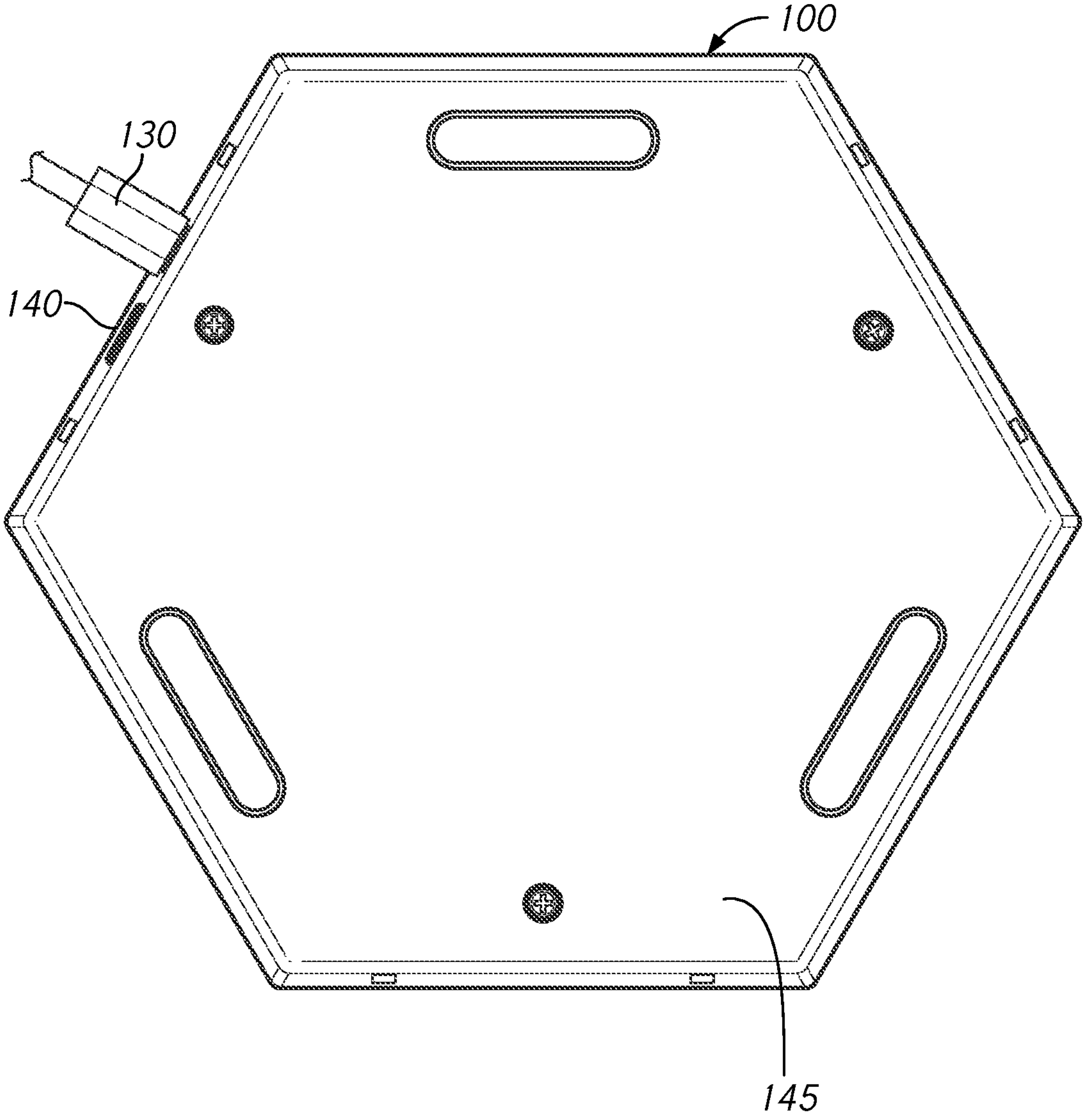
FIG. 5 is a rotated bottom view of the dispenser of FIG. 1.
Figure 6:
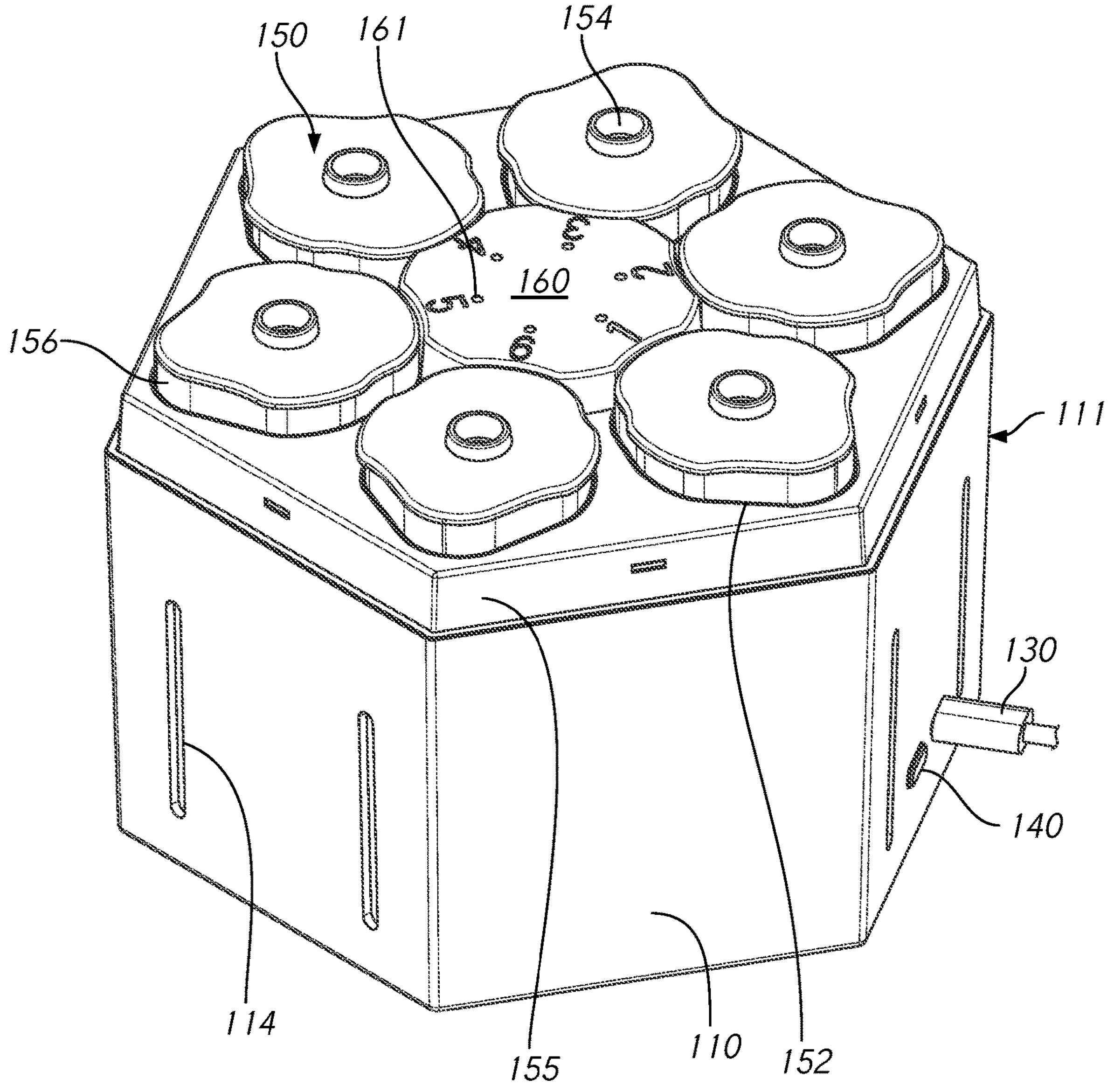
FIG. 6 is the dispenser of FIG. 1 with a cover removed.
Figure 7:
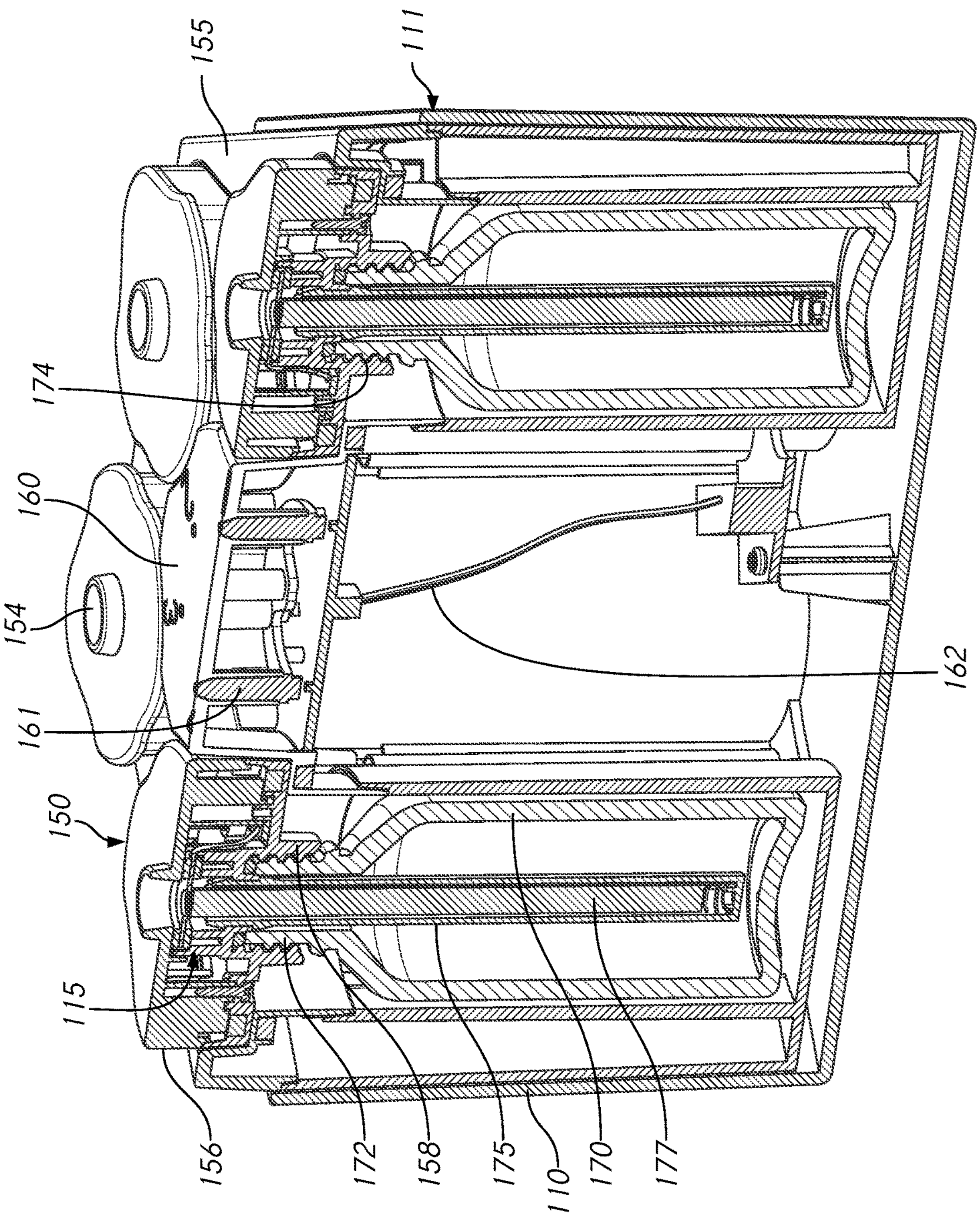
FIG. 7 is a cross-sectional perspective view of the dispenser of FIG. 6.
Figure 9:
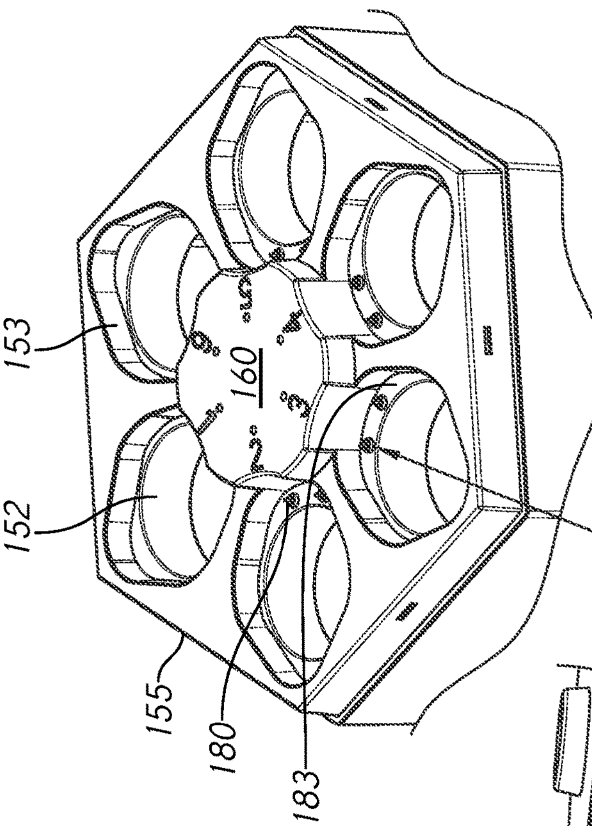
FIG. 9 is an enlarged, partial top perspective view of the dispenser of FIG. 6 highlighting a cover according to an embodiment.
Figure 10:
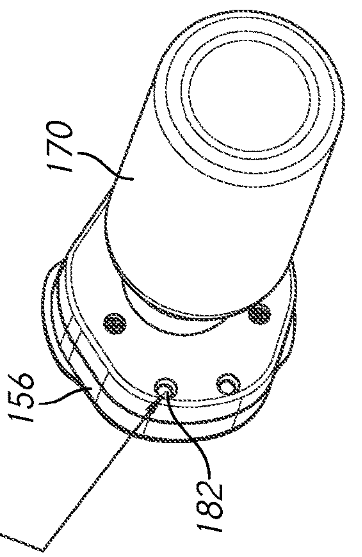
FIG. 10 is an isolated bottom perspective view of an atomizer cartridge exploded from a compartment of the dispenser of FIG. 6.
Figure 8:
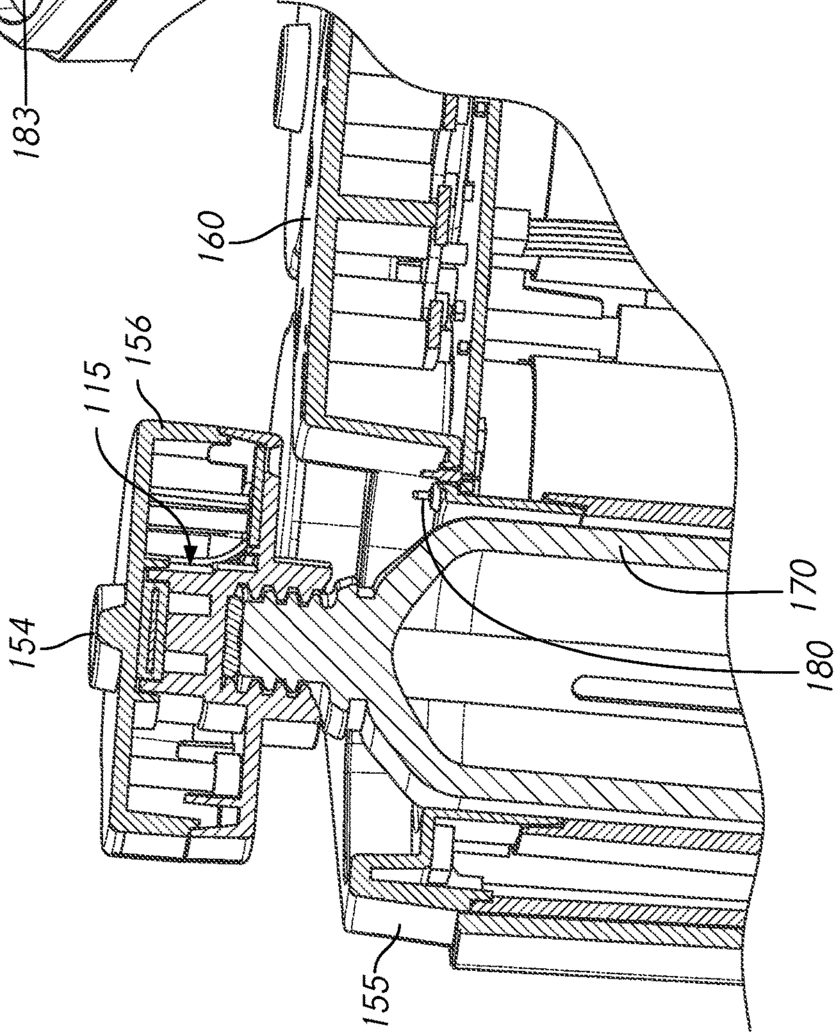
FIG. 8 is an enlarged partial view of the dispenser of FIG. 7.
Figure 11:
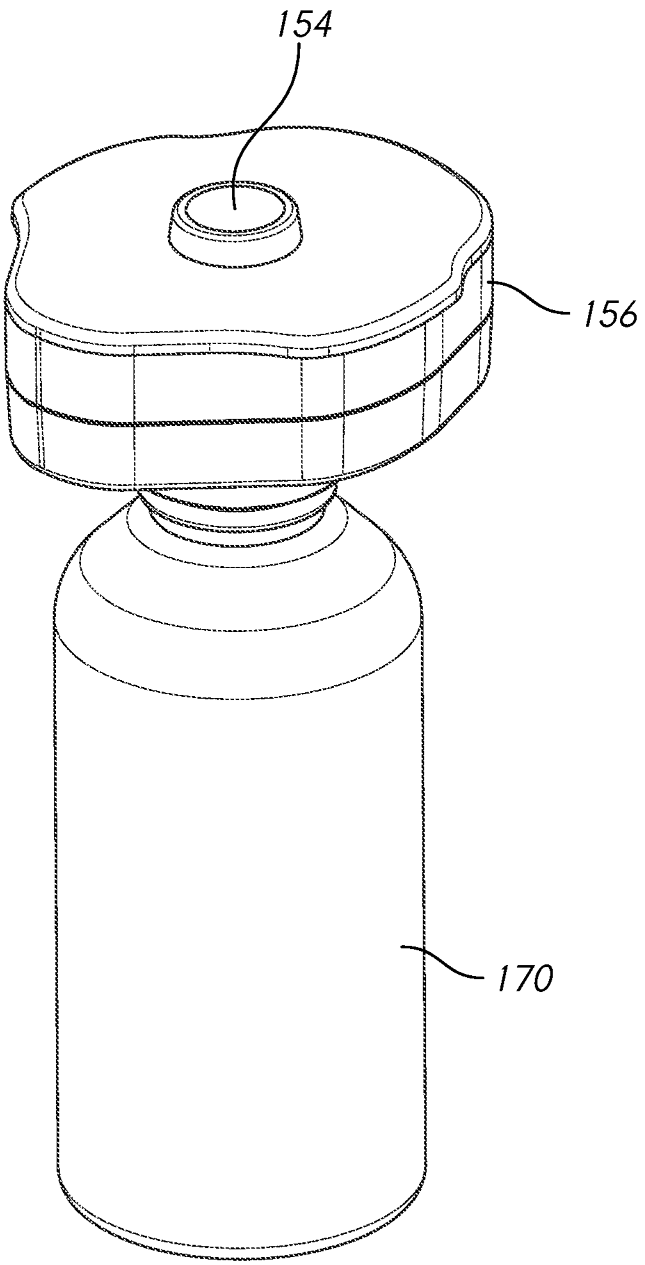
FIG. 11 is an isometric view of the atomizer cartridge of FIG. 10.
Figure 12:
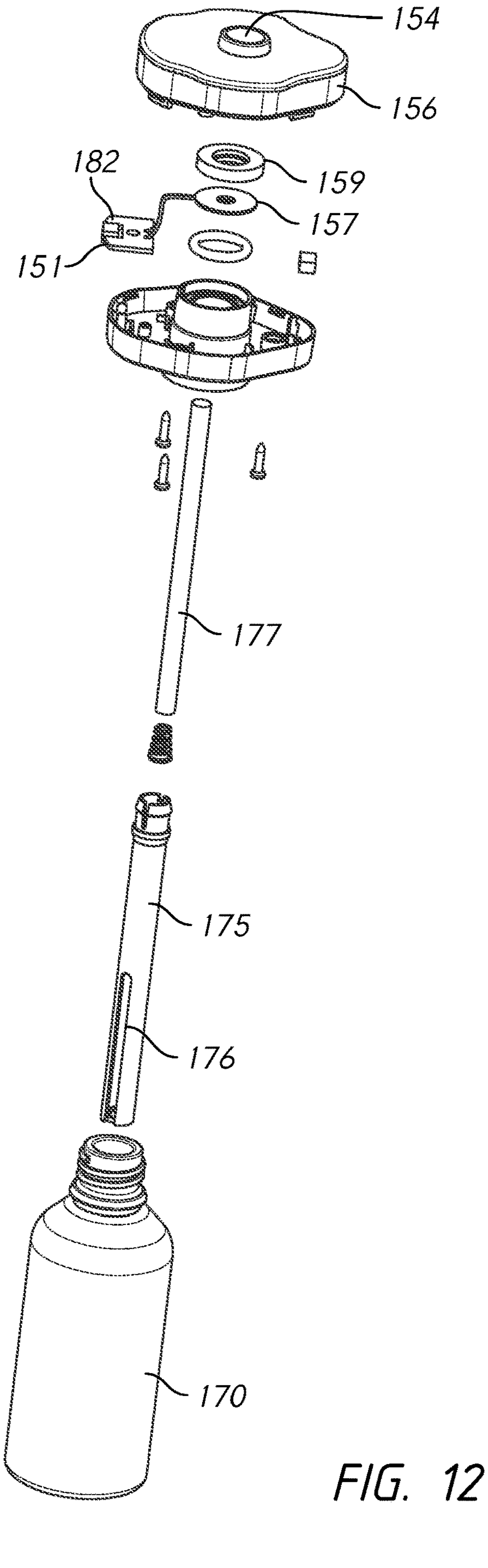
FIG. 12 is an exploded view of the atomizer cartridge of FIG. 11.
Figure 13:
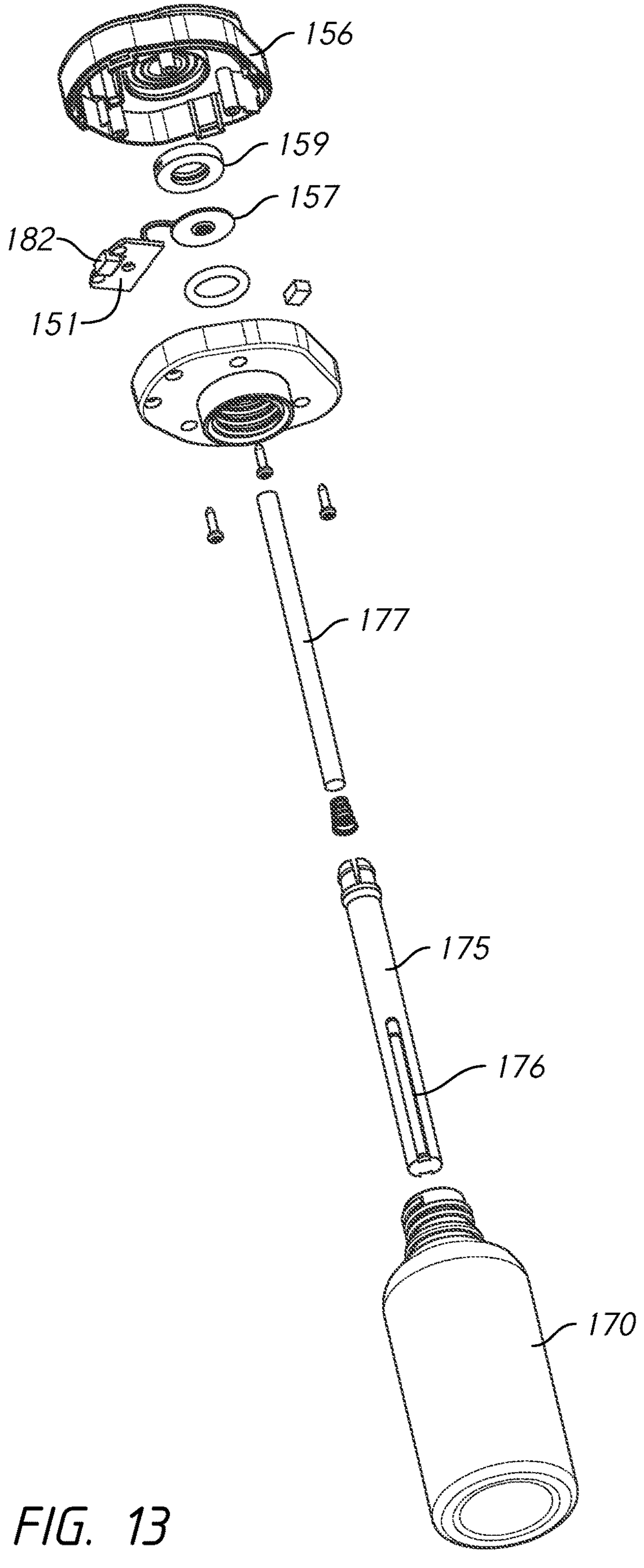
FIG. 13 is a bottom perspective view of the atomizer cartridge of FIG. 12.
Figure 14:
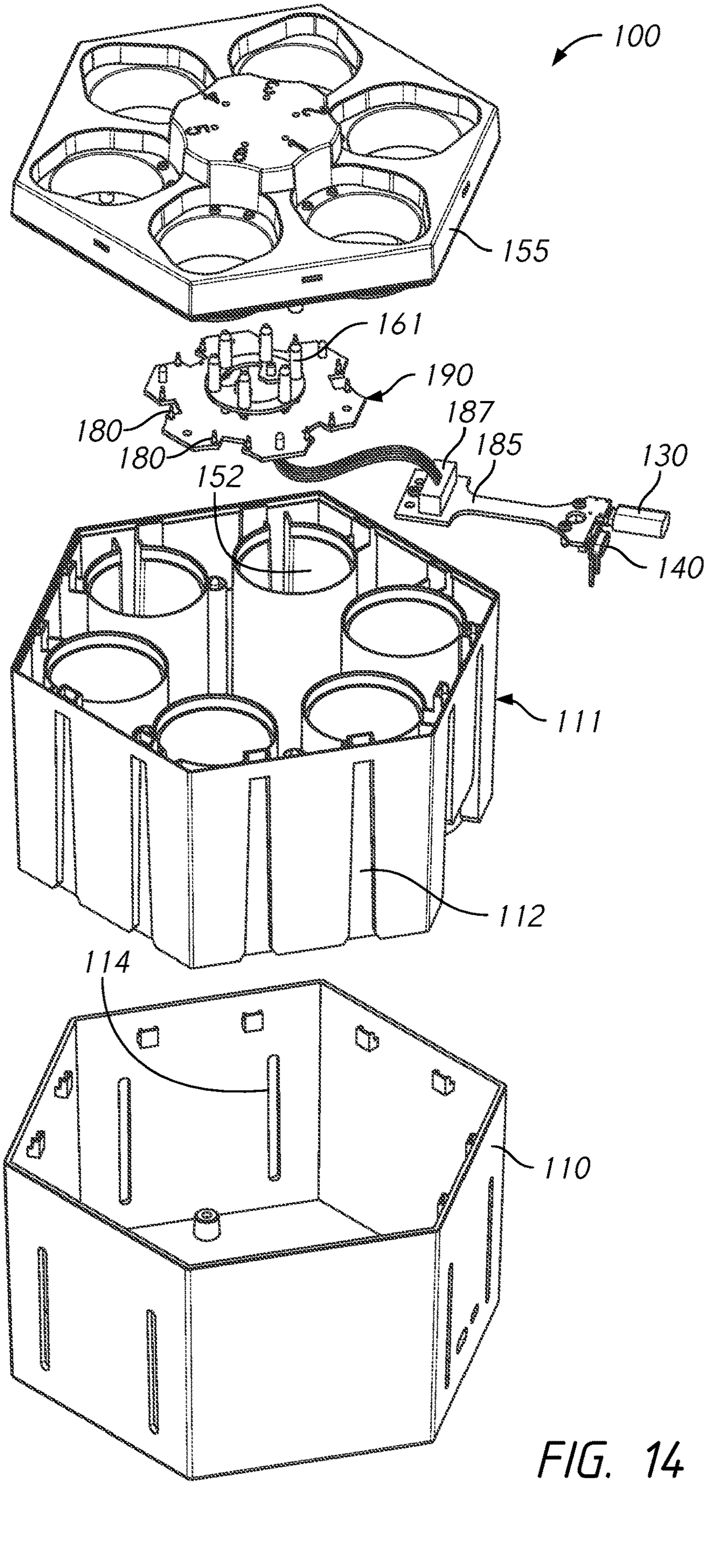
FIG. 14 is an exploded isometric view of the dispenser of FIG. 6 sans atomizer cartridges.
Figure 15:
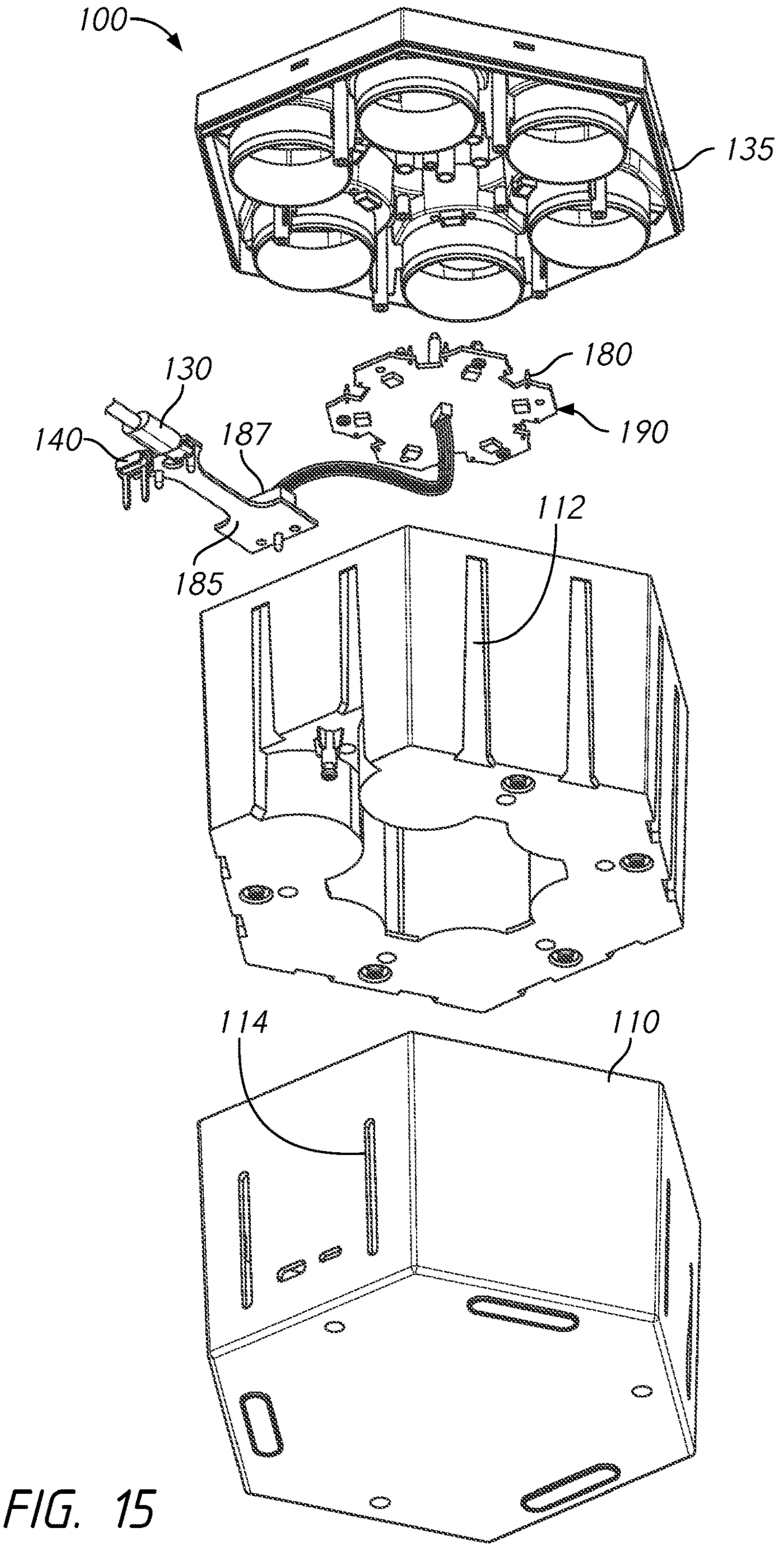
FIG. 15 is a bottom perspective view of the dispenser of FIG. 14.
Figure 16:
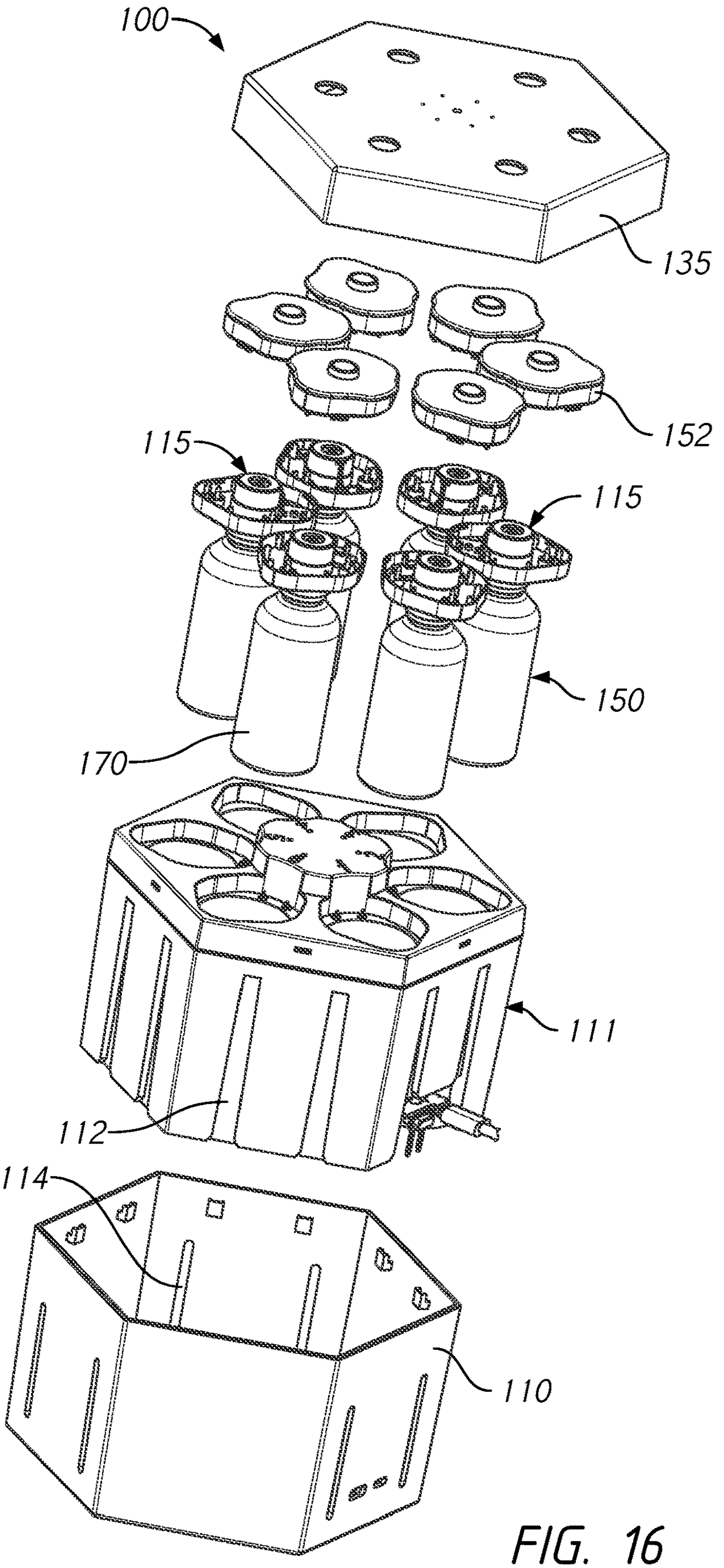
FIG. 16 is an exploded perspective view of the dispenser of FIG. 6.
Figure 17:
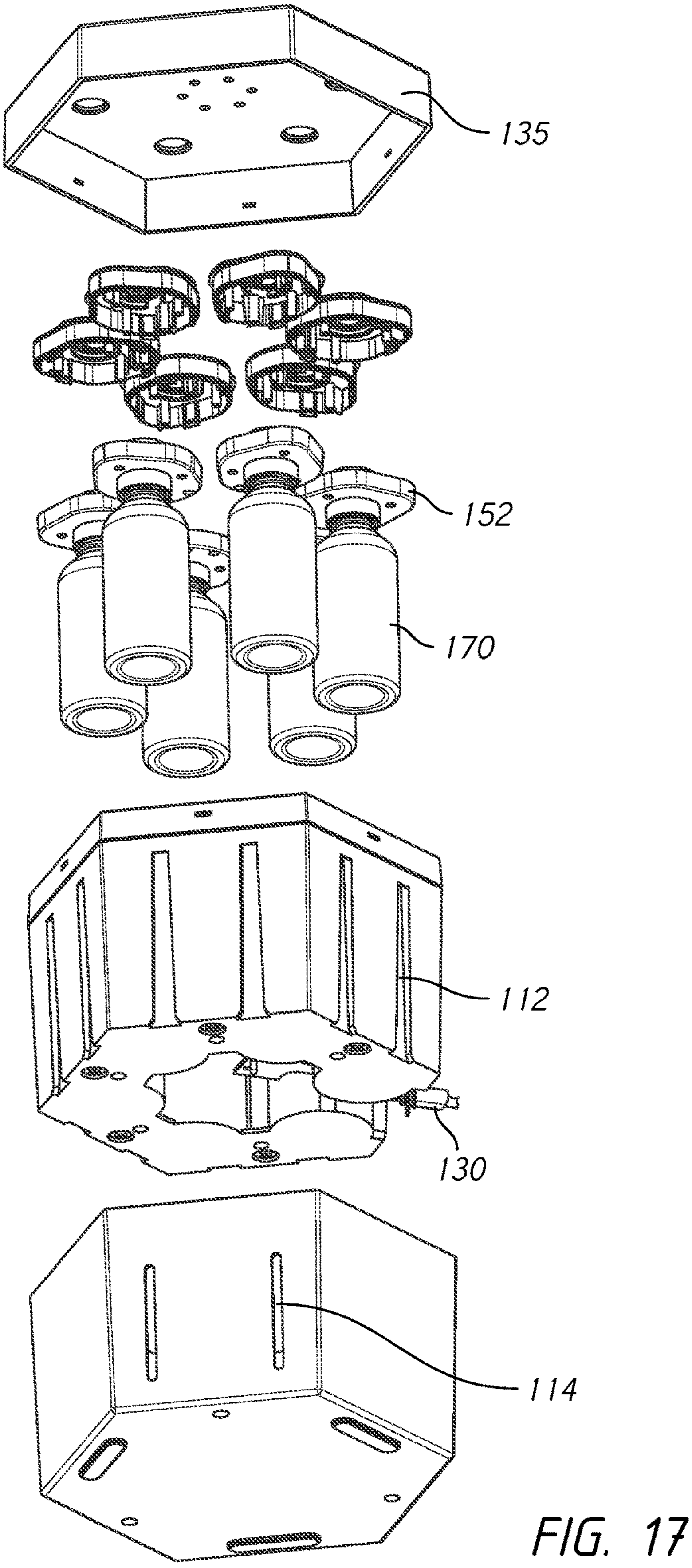
FIG. 17 is a bottom perspective view of the dispenser of FIG. 16.

Generally, embodiments of the subject technology provide a scent dispensing device, system, and process that is universal and can be used with any gaming system and any computer as well as any immersive environment (for example, a cinema or home theater system) where someone may also use the device while watching a movie giving them a more involved and immersive experience. As will be appreciated, the subject technology improves on other devices because the device is automated and will automatically release a scent based on some triggering criterium. In one illustrative embodiment, a processor chip continuously analyzes an audio stream from the environmental source, (for example, a game, movie, or other media player). The processor deduces events occurring in the game/movie from the sound stream, using various audio variables including amplitude, frequency, time period, wavelength, and velocity. The device may use artificial intelligence (A.I.) software to improve the accuracy of the device and its function over time. The release of a scent may be event based which may occur randomly (for example, not necessarily based on a predetermined scheduled event) or at unevenly distributed points in time within an audio signal. The device, for example, an atomizer, may include multiple cartridges holding different scents. When the system detects an event associated with a scent, the device cartridge releases the scent in response to the detected event. For example, if an event associated with an explosion occurs (which may occur during a combat scene or frequently in first person shooter games), every time (or sometimes) an explosion sound is detected, the device may release a smell that a user may associate with smoke and chemicals burning.

Definitions

Event: An "event" as used herein may mean an action, an environment, or an emotion that is detected.

Fluid: A "fluid" can refer to a gas or liquid.

Audio signal: An "audio signal" may mean either an analog signal or a digital signal.

Example Device

Referring now to FIGS. 1-7, a device 100 for automated dispensing of scents is shown according to an embodiment. The device 100 includes a housing 110 and a lid 135 that may cover a dispenser assembly 111. The dispenser assembly 111 may house one or more atomizers 150 (See FIG. 6). The lid 135 may include one or more ports 120 that are aligned with the nozzles 154 of respective atomizers 150. In some embodiments, the lid 135 may include central holes 125, which may be aligned with light pipes 161 (described further below) to provide light indicators. In some embodiments, the housing 110 may include one or more buttons 140. The button 140 is the example shown is a power button. Some embodiments include a jack or port (for example USB, audio, or other electronic communication port) for receiving a signal wire and plug 130. In the drawings, the jack/port is obscured by the connected plug 130. A base wall 145 is called out for sake of reference as the surface that may make contact with a floor or other support surface including a room wall or piece of furniture. Some embodiments may include a vertically longitudinal window 114 on the housing 110 that is in alignment with and disposed to show the fluid content level of one or more atomizers 150 in the device 100. For example, the dispenser assembly 111 may include windows 112 (See temporarily FIGS. 14-17) that are aligned with the windows 114.

FIGS. 6-10 show some of the internal elements of the device 100 according to an embodiment. The embodiment shown includes six atomizers 150 for illustrative purposes however it will be understood that embodiments may include more or less atomizers 150. The atomizers 150 may be held in respective slots 152. In some embodiments, the atomizers 150 may include a dispenser 115 configured to emit a fluid as a scent. In one embodiment, the dispenser 115 may be covered by a removable head 156 that may dispense the fluid by mechanical and/or electronic means. The heads 156 may rest on a seat module 155 and may protrude therefrom. In some embodiments, the shape of the heads 156 may be arbitrary and the seat module 155 may include keyed openings 153 configured to match the keyed shape of the heads 156. Some embodiments may include a raised boss 160 that may be centralized on the seat module 155. The raised boss 160 may include numbering or some other indicia that is correlated to each of the atomizers 150. As may be appreciated, when the atomizers 150 are inserted into their respective slots 152, users may be able to match the scent from an atomizer to the numbered slot, which can then be used when programming which atomizer to be dispensed in association with an event. A light pipe 161 may be positioned next to each indicium. The light pipe 161 may extend from the top surface of the raised boss 160 into the interior of the raised boss 160. Wiring 162 may connect each of the light pipes 161 to a power source. The light pipes 161 may provide a visual indicating an availability status of each atomizer 150.

Each atomizer 150 may include a cylindrical cartridge 170 connected to dispenser 115 and heads 156, which may be configured to slide into respective slots 152. In some embodiments, the neck 172 of the cartridge 170 may include a male treaded boss configured to mate with a female threaded boss 174 of removable head 156. The head 156 may include a top cap that is removable from a bottom half of the head. In some embodiments, the seat module 155 includes a pair of pins 180 (which may be for example, electrifying vibration needles) positioned on an inset lip 183 proximate the top of the slot 152. An underside surface of the heads 156 may include a conductive contact 182 aligned to receive the pins 180 when the atomizers 150 are positioned in their respective slots 152. As may be appreciated, some embodiments only allow the heads 156 to be oriented so that the contacts 182 align with the pins 180 because of the keyed openings/heads configuration.

Referring now to FIGS. 7-13 additional details of the internal elements of an atomizer 150 are shown according to an embodiment. In some embodiments, the atomizers 150 may include a mechanical, electro-mechanical, or electronic dispenser mechanism in the head 156. Generally, the cartridge 170 includes an inner chamber for housing a fluid that is selected prior to use based on having a scent that is reminiscent or associated with a type of event. For example, an event detected as an explosion, a firearm discharge, a fire, or cigarette burning may use a fluid that smells like smoke. For example, liquid smoke and other oils may have varieties of smokiness that can be used to replicate the olfactory experience of the aforementioned burning related events. Other events that are examples of events detected include water associated environments (rain, saltwater bodies, sea spray, river rapids, etc.). Events that are detected may be static or active. An environment may be an example of a static event. Another active event example may be for example, the peeling of an orange that triggers release of a scent that reminds one of citrus.

As an illustrative embodiment, the atomizer 150 is shown as an electronic device. A tube 175 may be positioned in the cartridge 170 interior. The cartridge 170 may be transparent so that the level of fluid can be seen through the window 112 of the dispenser assembly 111 and further visible through the level indicator window 114 of housing 110. A wick 177 may sit concentrically within the tube 175 to draw the fluid up into the head 156. The tube 175 may include a window 176 to expose the fluid in the cartridge 170 to the wick 177. The upper tip of the wick 177 may be positioned through a center of or proximate a metallic heating element 159 (which in this example is shown as a ring shaped element). In some embodiments, an electronic conductor 157 may sit under (or at least generally in contact with) the heating element 159. Current may be provided to the electronic conductor 157 through the contacts 182 which may sit on pads 151.

Referring now to FIGS. 14-17, exploded views of the device 100 are provided that show the electronic connection to the contacts 182 that are shown in previous figures. A command signal may be provided through the plug 130. A ribbon circuit 185 (or PCB or other wired connection) may transfer the command signal to a controller circuit 190. In some embodiments, the command signal is routed through a multi-line plug 187 connected between the ribbon circuit 185 and the control circuit 190 with each wire from the plug 187 being routed to a respective pin 180 and/or a light pipe 161. In embodiments that use a wireless connection, the control circuit 190 may include a wireless transceiver to receive command signals and/or return feedback signals from the controller/computer source.

System

Figure 18:
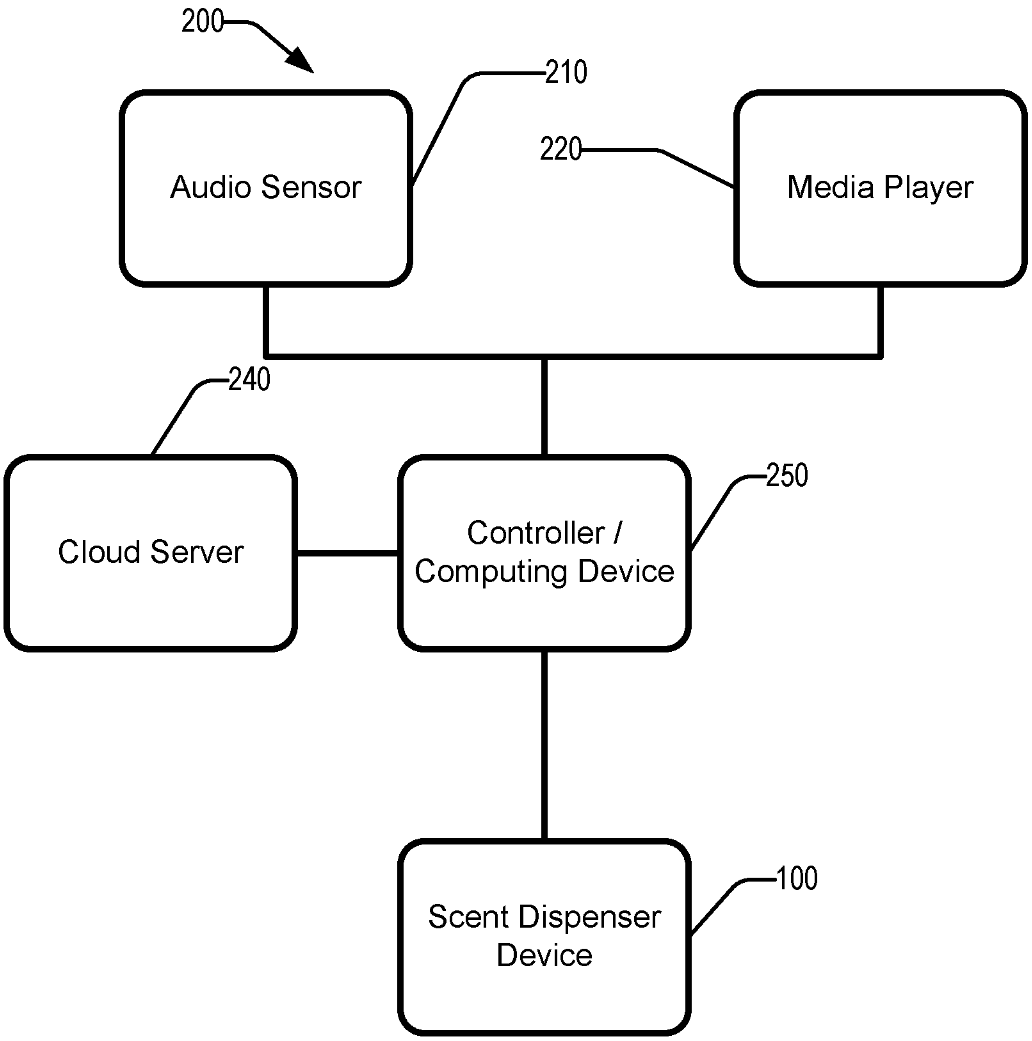
FIG. 18 is a block diagram of a system for automated dispensing of a scent in accordance with an illustrative embodiment of the subject technology.

Referring now to FIG. 18, a system 200 for automated dispensing of scents if shown according to an embodiment. The system 200 includes a scent dispenser device 100 connected to a dedicated controller or a computing device 250. The connection between the device 100 and the controller/computing device 250 may be hardwired (for example, via plug 130 described above) or via a wireless connection. When a computing device 250 is used, the computing device 250 may be a desktop or terminal PC, a computing tablet, a gaming console, media player, a smart phone, or a virtual reality system. Some embodiments may include an audio sensor 210 (for example a microphone) placed in an open environment (for example, a public or home theater) or may use a digital audio stream obtained directly from a media player 220. The media player 220 may be a gaming console, a smart television, a computing device, a programmable consumer device, a virtual reality system, or a retrofit media player such as a DVD player, laser disc player, etc.

Figure 19:
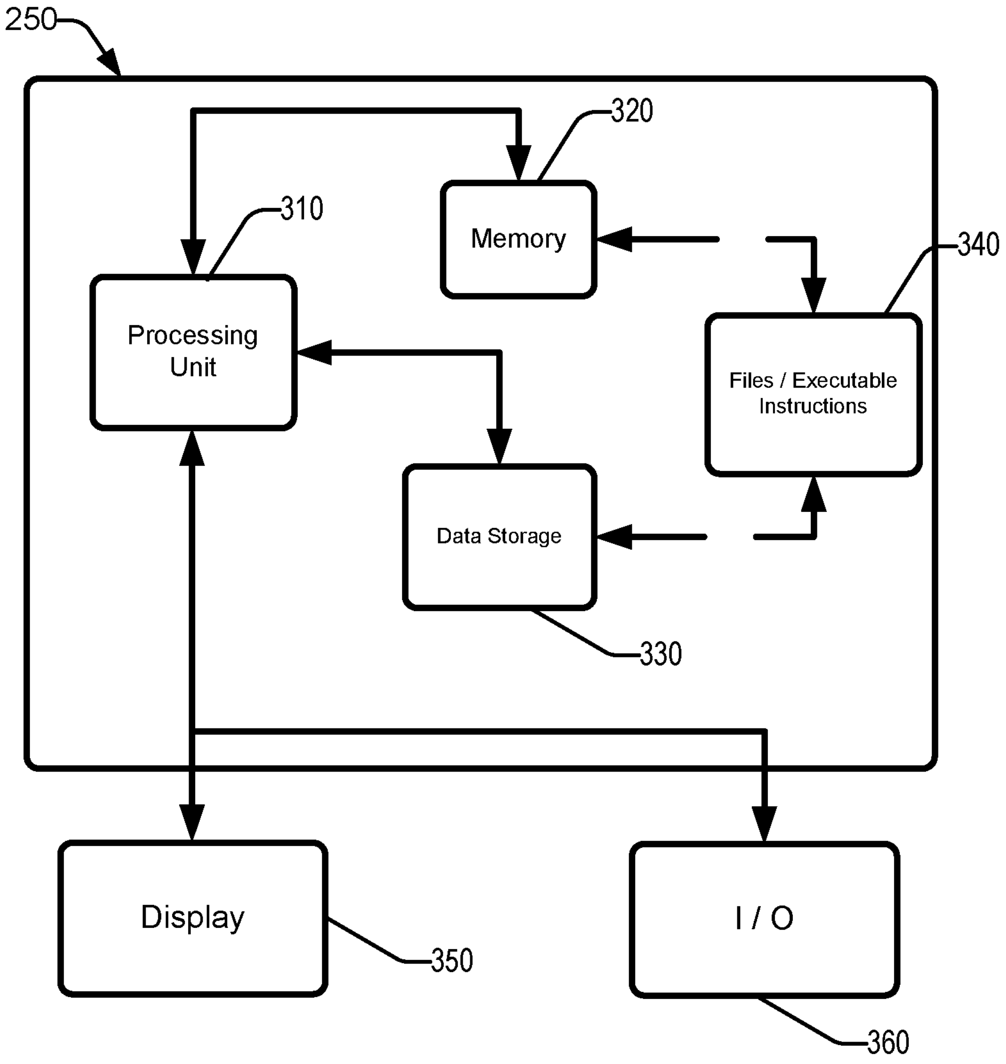
FIG. 19 is a is a block diagram of a controller or computing device for automated dispensing of scents in accordance with an illustrative embodiment of the subject technology.

Referring temporarily to FIG. 19, an example of computing device 250 is shown in block form consistent with embodiments of the controller or computing device 250. It will be understood that a "computing device" may serve different roles depending on the need in the system or depending on the step being performed in a process. For example, in the role of a cloud server, a host server, or an online platform server, a computing device 250 may implement for example the functions related to backend processes described above and further below with respect to FIG. 20. As will be understood, the user device may generally provide frontend aspects of the system. In some embodiments however, the frontend computing device may perform one or more of the backend steps where possible.

The components of the computing device 250 may include, but are not limited to, one or more processors or processing units 310, a system memory 320, data storage 330, a computer program product 340 having a set of program modules including files and executable instructions, and a bus system that couples various system components including the system memory 320 to the processor (s) 310. The memory storage 320 may store for example, fluid names, their scent profiles, cartridge numbers, current fluids in cartridges, user selected events, an event catalog, scent dispense times and frequencies, current fluid levels, and event audio signal profiles.

The computing device 250 may be described in the general context of computer system executable instructions, such as the program modules which represent a software embodiment of the system. The program modules generally carry out the functions and/or methodologies of embodiments as described above and below. The computing device 250 may typically include a variety of computer system readable media. Such media could be chosen from any available media that is accessible by the computing device 250, including non-transitory, volatile and non-volatile media, removable and non-removable media for use by or in connection with an instruction execution system, apparatus, or device. A computer readable storage medium may be, for example, but not limited to, an electronic, magnetic, optical, electromagnetic, infrared, or semiconductor system, apparatus, or device, or any suitable combination of the foregoing. The system memory 320 could include one or more computer system readable media in the form of volatile memory, such as a random-access memory (RAM) and/or a cache memory. By way of example only, the data storage system 1330 may read from and write to a non-removable, non-volatile magnetic media device. The system memory 320 may include at least one program product 340 having a set of program modules that are configured to carry out the functions of embodiments of the invention in the form of computer executable instructions. The program product/utility 340 may be stored in the system memory 320 by way of example, and not limitation, one or more application programs, other program modules, and program data. Some embodiments may generate an electronic user interface (viewable and controllable from the display unit 350) that may allow the user to enter the scent dispensing related information.

The computing device 250 may communicate with one or more external devices including for example, a peripheral form of the electronic display 350 which may in some embodiments be configured for tactile response as in a touch screen display. User input into the display 350 may be registered at the processor 310 and processed accordingly. Other devices may enable the computing device 250 to communicate with one or more other computing devices, either by hardwire or wirelessly. Such communication can occur via Input/Output (I/O) interfaces/ports 360.

The computing device 250, through the I/O interface/ports 1360, may communicate with one or more networks such as a local area network (LAN), a general wide area network (WAN), and/or a public network (e.g., the Internet) via a network adapter as is commonly known in the art. Each of the operating system, one or more application programs, other program modules, and program data or some combination thereof, may include an implementation of a networking environment. In some embodiments, the computing device 250 may be a cloud computing node connected to a cloud computing network (for example cloud server 240 shown in FIG. 18). The computer computing device 250 may be practiced in distributed cloud computing environments where tasks are performed by remote processing devices that are linked through a communications network. In a distributed cloud computing environment, program modules may be located in both local and remote computer system storage media including memory storage devices.

Referring back now to FIG. 18, some embodiments include an Android or iOS smart phone app (which maybe a form of the program product 340) that allows the consumer/user to configure the device with Wi-Fi credentials and short range protocol pairing, a local area network connection. or a cellular telephony connection. The app may include one or more user interfaces that provide selectable buttons or fields where the user can select a cartridge number and associate a scent with a selectable event. Some embodiments of the app may notify the user whenever a scent cartridge is low. Some embodiments of the app provide an electronic merchant interface to buy a replacement cartridge with one tap and the phone app.

Hardwire embodiments may include a WiFi/BLE, USB, Audio Input plug 130 whose other end is plugged into the HDMI port of a computing device 250 or gaming console 220 (or other entertainment device) to capture the audio stream and a USB plug to power the adaptor. For a computer, the same adaptor is plugged into the HDMI port on the computer as well and the USB to power the adaptor but there may also be an audio out plug that plugs into the audio output on the back of a computer that is a splitter connection so the audio is still accessible to the user for speakers or other outputs. The adaptor captures the sound stream and transfers that audio stream to the controller/computing device 250 in a transmission to the cloud server 240 where an audio detection software resides. The cloud server 240 may process the audio signal in real-time and determine when an event in the audio signal matches one of the user selected events. The cloud server 240 may determine which cartridge in the local device 100 includes the fluid matched with the identified event and sends a command signal to the controller/computing device 250 to trigger the identified atomizer of the cartridge.

Figure 20:
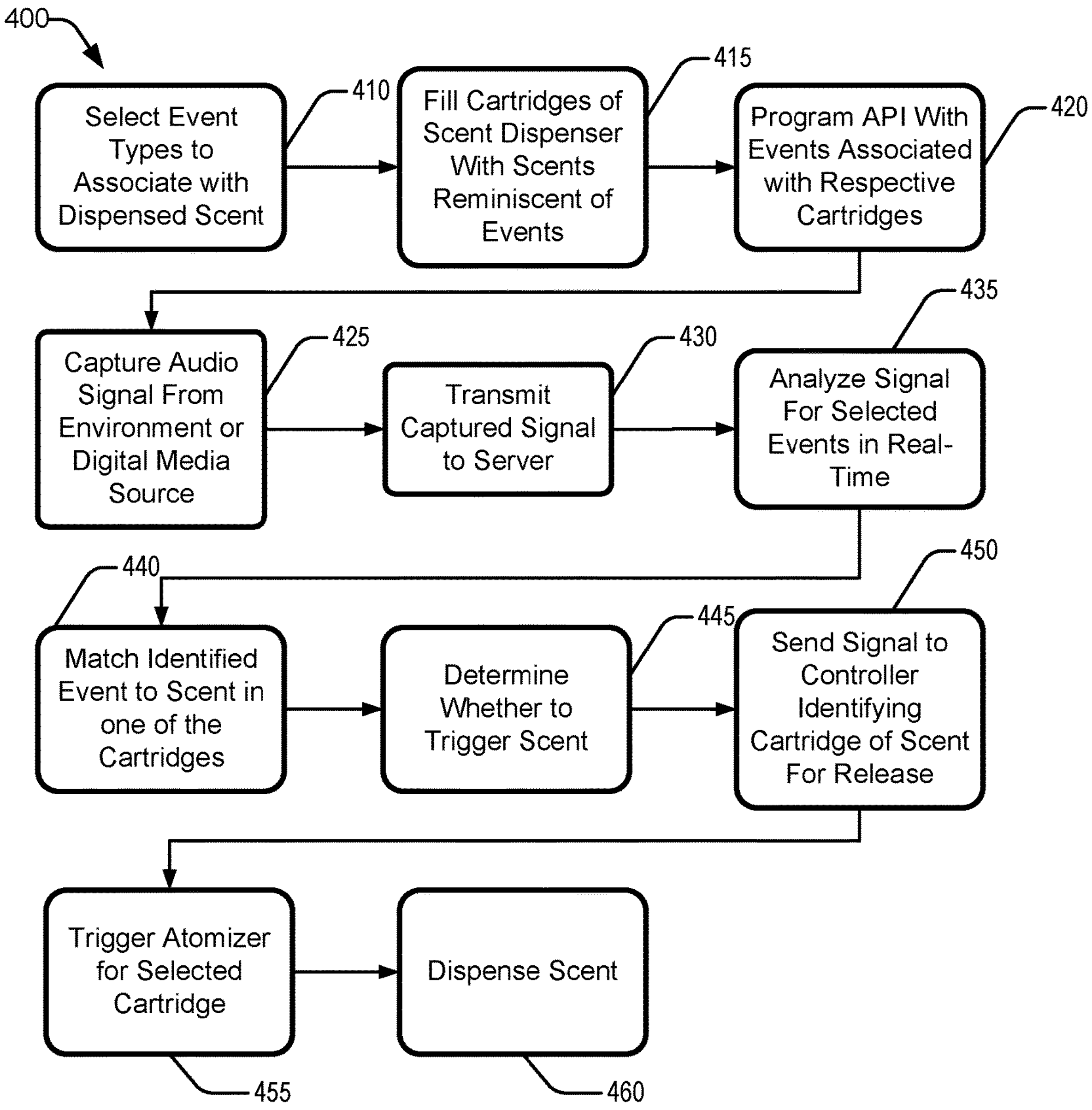
FIG. 20 is a flowchart of a process for automated dispensing of scents for an immersive experience in accordance with an illustrative embodiment of the subject technology.

Referring now to FIG. 20, a process 400 for automated dispensing of scents for an immersive experience is shown according to an embodiment. The process 400 includes some of the general actions described above and is provided for additional detail. In block 410, user selected event types (for example, explosions, urban traffic, terrain environments (forest, oceanside, farmland, etc.), etc.) may be received by a computing device input. The computing device may provide a list of fluid names to be used for the selected events. The fluid carrying cartridges may be filled, in block 420, with the fluids and set into respective dispenser slots. The API UI may receive which cartridge numbers have which fluid scents loaded.

As audio is playing, the system may capture, in block 425 the audio signal from the environment (or extract the signal from a digital stream). The captured signal may, in block 430, be transmitted to the cloud server 240. At block 435, a processor in the server 240 (or in some embodiments, the processor 310 directly) may analyze the audio signal for events that match the user selected events.

Analysis

Embodiments may handle the analysis of the audio signal in different ways. In one embodiment, an artificial intelligence (AI) component may be configured to identify events in the audio signal, identify precursors and patterns associated with events, and predict upcoming events to occur in the audio signal based on the other events and data analyzed from the audio signal as well as historical prediction models. In one embodiment, the different types of detected audio events occur at arbitrary times within the audio signal. There may be no set schedule to dispense a scent during the playback of a movie or engagement in a video game (or other immersive experience) so that an artificial intelligence engine (described in more detail below) predicts when an event is likely to occur and determines via past experience whether the dispense of a scent under current conditions is positively received by end users. In some embodiments, the identified event occurs multiple times in the audio signal and the cartridges may be triggered unevenly based on one type of event occurring more often. In some embodiments, the identified event is detectable at unevenly spaced multiple points in time and the selected scent is dispensable at any of the multiple points in time. The server may analyze the current frequency of a detected event and determine whether continuous dispensing of the scent may be overwhelming or generally uncomfortable for an end user.

At block 440, the processor may match the identified event to one of the scents loaded into the dispenser. At block 445, the processor may determine whether to trigger dispense of the scent. As previously mentioned just above, in conditions that include too frequent operation of a cartridge or for example, a scenario where one scent may mask another (rendering the weaker scent's dispense irrelevant) or for example, a mix of two scents is known to produce an offensive or unintended smell, the operation one or more atomizers may be temporarily overridden. When the processor determines that the dispense of scent is favorable, in block 450, a command signal identifying the cartridge(s) carrying the right fluids for a scent is transmitted. Some embodiments may mix fluid atomization to produce a desired scent. The processor, A.I. engine, and/or server 240 may include instructions to determine a proper mix of fluids to create some scents. In block 455, the atomizer(s) for the selected cartridge(s) may be triggered. In block 460, the scent may be dispensed into the environment. The volume of scent produced may be based on the number of end users experiencing the media being played.

Artificial Intelligence

Figure 21:
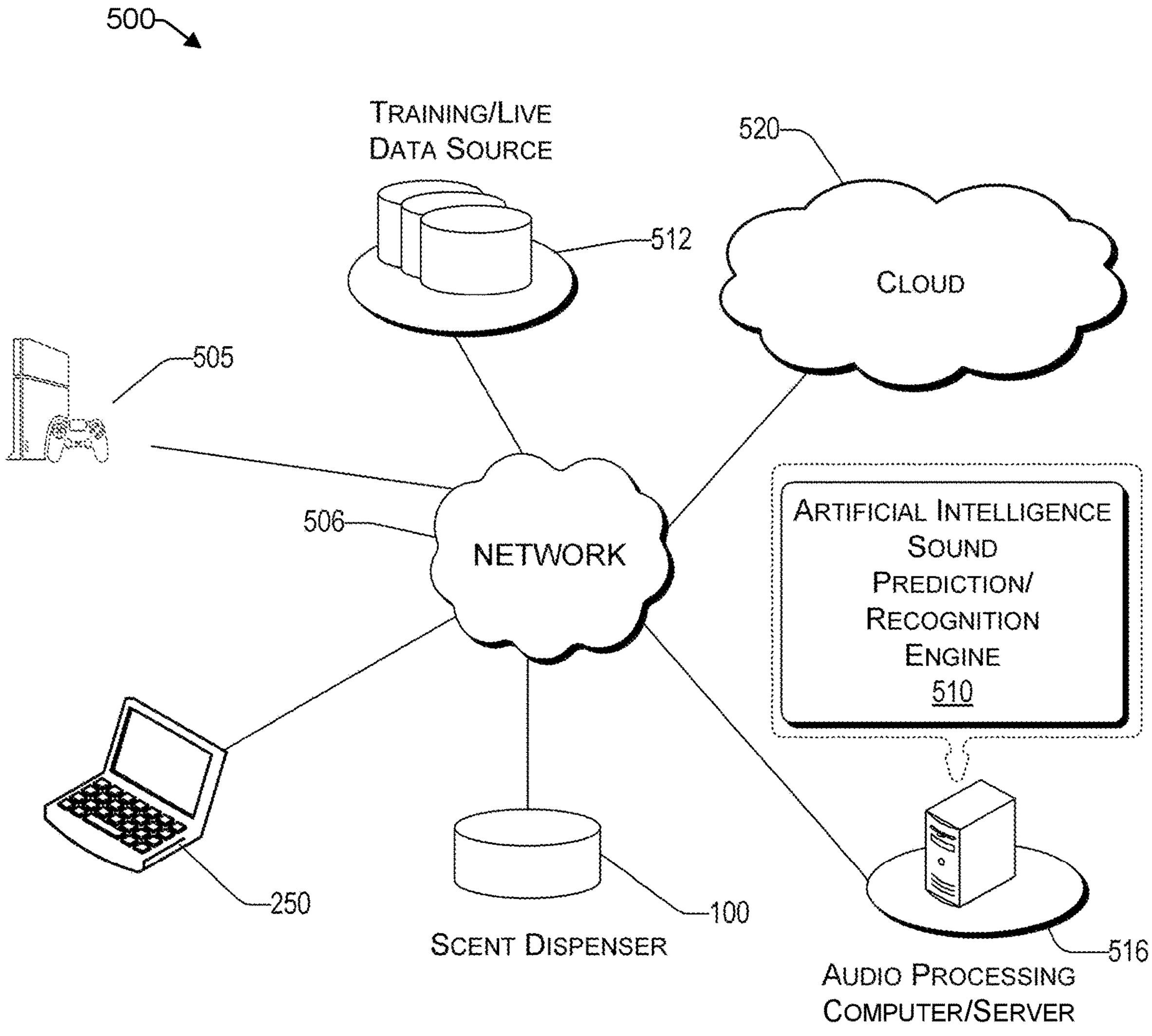
FIG. 21 is a block diagram of an architecture for training and real-time operation of an artificial engine to identify and predict events in an audio signal in accordance with an illustrative embodiment of the subject technology.

FIG. 21 illustrates an example architecture 500 for automatically dispensing a scent into an environment using artificial intelligence-based predictions and determinations. Architecture 500 includes a network 506 that allows the other elements in the architecture to communicate with each other. Other elements that are connected to the network 506 may include for example, the scent dispenser 100, a computing device 250, a gaming console 505 (or other digital audio/visual media device), a data source 512, an audio processing computer/server 516, and the cloud 520.

The network 506 may be, without limitation, a local area network ("LAN"), a virtual private network ("VPN"), a cellular network, the Internet, or a combination thereof. For example, the network 506 may include a mobile network that is communicatively coupled to a private network. The network 506 allows an artificial intelligence sound prediction/recognition engine 510 (sometimes referred to simply as the "AI engine 510"), which is a software program running on the audio processing computer/server 516, to communicate with the data source 512, computing device 250, gaming console 505, and the cloud 520, to provide data processing of a detected/received audio signal. The data source 512 may provide data from historically recorded past audio signals and from database sources including for example, Internet pages, external databases, internal databases, and corpora of documents/files that will be used for one or more techniques described herein. In an exemplary embodiment, artificial intelligence is one technique used for processing the data to build predictive models and in some embodiments, generate predictions of upcoming audio events. In one embodiment, the data processing is performed at least in part on the cloud 520.

The audio signal data may be a digital audio stream provided by the gaming console 505 or picked up by a sensor (for example, a microphone detecting the analog output of a speaker playing the sound track from a movie or other audio/visual source). The audio signal may be received by the computing device 250 which may process the received signal for use by the AI engine 510. Processing the audio signal may include parsing the signal into different data points, which may be provided to the data source 512 for storage and retrieval. Since some signals may include overlapping sounds, the computing device 250 may separate different sound signatures from each other for further analysis by the AI engine 510.

The AI engine 510 may include models trained to predict upcoming events and identify events in an audio stream based on the historical data provided by the data source 512. As an example, the AI engine 510 may identify various actions, terrains, words, and other sound signatures from the data points in the audio signal. The prediction of upcoming events may be based on identifying precursor events and patterns of sounds from within the audio signal. As an illustrative example, in the context of gaming users playing a first-person shooter, the AI engine 510 may predict a frequency of gunfire based on player's historical patterns of triggering a weapon. Moreover, the AI engine 510 may predict larger explosions from precursor events including for example, words uttered by players (for example, "fire in the hole" which may provide a forewarning of a grenade being thrown or launched) or patterns of gun fire that precede an explosive device being used. As such, the AI engine 510 may provide predictions of different events that are about to occur within milliseconds of the actual event in the audio signal occurring. The prediction may be sent to the computing device 250 which may trigger the scent dispenser to dispense a smell reminiscent of smoke and/or lit gunpowder. It should be understood that while the preceding example described the context of a first person shooter game, this example was illustrative only and the AI engine 510 may be configured to recognize and predict other events associated with scents (for example, a person traversing through a terrain such as a forest, near a body of water, farmland, an urban setting, etc.

While the data source 512 and the AI engine 510 are illustrated by way of example to be on different platforms, it will be understood that in various embodiments, the data source 512 and the audio processing computer/server 516 may be combined. In other embodiments, these computing platforms may be implemented by virtual computing devices in the form of virtual machines or software containers that are hosted in the cloud 520, thereby providing an elastic architecture for processing and storage.

Figure 22:
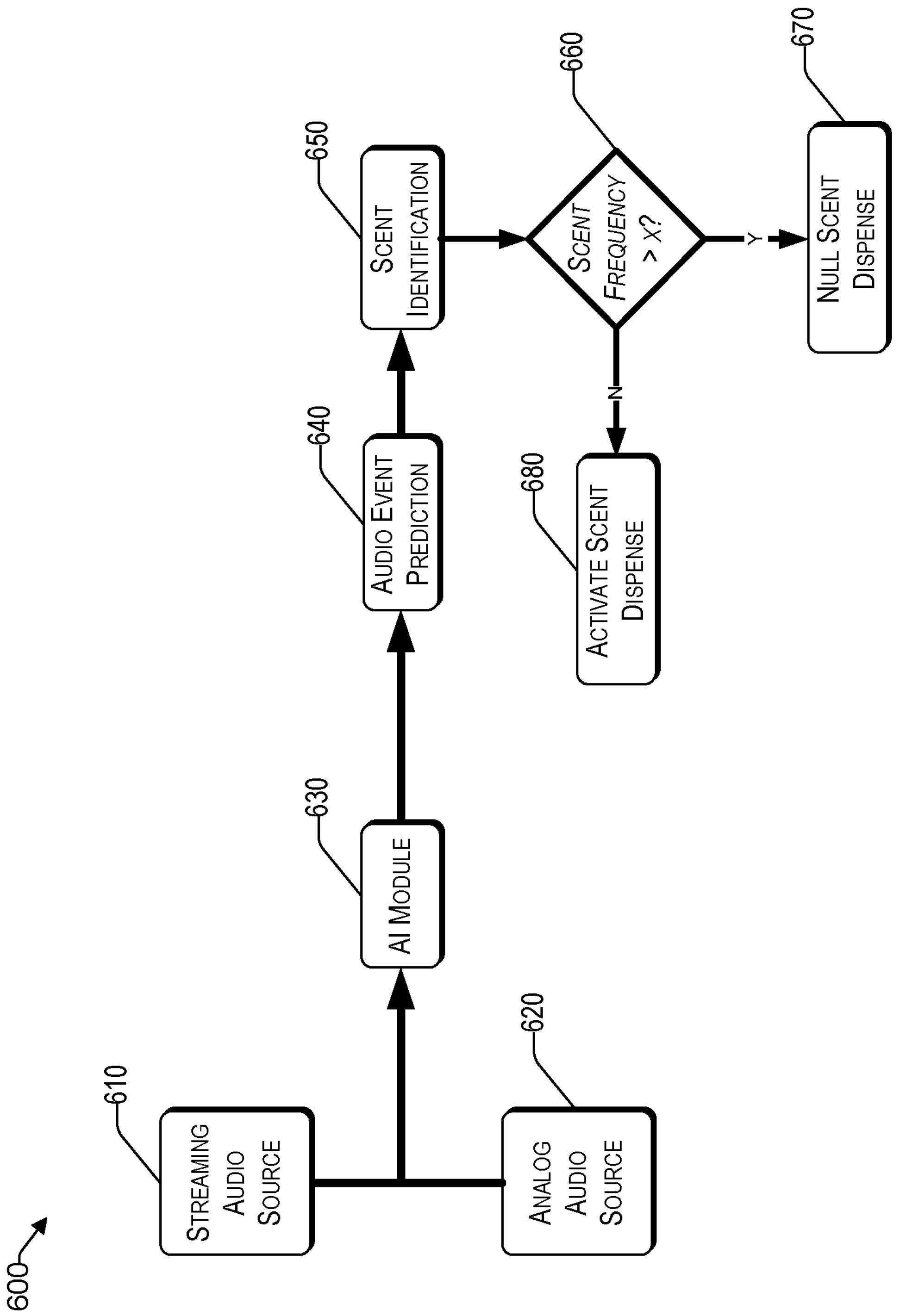
FIG. 22 is a flowchart of a method for automatically dispensing a scent into an environment based on prediction of an event via artificial intelligence in accordance with an illustrative embodiment of the subject technology.

FIG. 22 shows a method 600 of automatically dispensing a scent into an environment based on an AI process. The AI process may be performed by an AI module 630 (for example, the AI engine 510 of FIG. 21). In general, the AI module 630 may receive an audio signal from either a streaming audio source 610 or an analog audio source 620. The audio module 630 may process the audio signal to predict 640 events that will occur further into the future of the audio signal. For predicted events, a computing device (for example, the computing device 250) may identify a label associated with the predicted event. The label may be used to identify 650 scents that correlate with the predicted event. In some embodiments, the computing device may determine 660 whether the scent that will be dispensed in relation to the occurrence of the predicted event has been (or will be) dispensed too frequently (for example, according to a threshold value of frequency) within a time window or has been released to close to a last dispense. If the threshold value is exceeded, then the computing device may void 670 the dispense of scent (for example, by ignoring the predicted event signal, temporarily rendering the atomizer associated with the event inactive, or otherwise preventing the atomizer from operating for the time being). Otherwise, the atomizer for the scent dispenser is activated 680 to release the scent.

As will be appreciated, a person will now be able to experience scents related to activities occurring in the game/movie that will be released automatically when germane to the current scene being experienced. Currently users have sight, hearing, and touch senses in the gaming experience but lack smell and taste from the five primary senses. Smell actually also has somewhat of a taste element so for the first time, a person can experience all five primary senses when they are gaming.

As will be appreciated by one skilled in the art, aspects of the disclosed invention may be embodied as a system, method or process, or computer program product. Accordingly, aspects of the disclosed invention may take the form of an entirely hardware embodiment, an entirely software embodiment (including firmware, resident software, micro-code, etc.) or an embodiment combining software and hardware aspects that may all generally be referred to herein as a "module", "circuit", or "system." Furthermore, aspects of the disclosed invention may take the form of a computer program product embodied in one or more computer readable media having computer readable program code embodied thereon.

Aspects of the disclosed invention are described above with reference to block diagrams of methods, apparatus (systems) and computer program products according to embodiments of the invention. It will be understood that each block of the block diagrams, and combinations of blocks in the flowchart illustrations and/or block diagrams, can be implemented by computer program instructions. These computer program instructions may be provided to the processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks in the figures.

Those of skill in the art would appreciate that various components and blocks may be arranged differently (e.g., arranged in a different order, or partitioned in a different way) all without departing from the scope of the subject technology. The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects.

What is claimed is:

1. A method for automatically dispensing a scent into an environment, comprising:

continuously detecting by a sensor or a computer processor, an audio signal in the environment;

forwarding data points in the audio signal to an artificial intelligence engine;

identifying, by the artificial intelligence engine, one or more precursors and patterns from the audio signal, associated with an event;

predicting by the artificial intelligence engine, an occurrence of the event based on the precursors and patterns identified in the audio signal;

forwarding the prediction to a computing device or a controller communicatively coupled to a scent dispenser;

identifying, by the computing device, a scent correlated to the event; and operating by the computing device or the controller, a dispense of the identified scent by the scent dispenser into the environment in association with a predicted occurrence of the event; and determining by the computing device or controller, whether a frequency of dispense of the identified scent exceeds a threshold value within a window of time.

2. The method of claim 1, wherein the audio signal is an analog signal.

3. The method of claim 2, wherein the analog sound is received from a speaker playing a sound track from a playback of an audio/visual media.

4. The method of claim 1, wherein the audio signal is a digital audio stream.

5. The method of claim 4, wherein the digital audio stream is received from one of a gaming console, a virtual reality system, a smart phone, a smart television or display, and a personal computer.

6. The method of claim 1, further comprising preventing the scent dispenser from dispensing the scent in the event the threshold value is exceeded.

7. The method of claim 1, wherein the scent is selected based on a smell reminiscent of the event.

8. The method of claim 1, wherein the identified event occurs multiple times in the audio signal.

9. The method of claim 1, wherein the predicted event occurs at an arbitrary point in the audio signal.

10. The method of claim 1, wherein the predicted event is a gun fire or explosion and the scent dispensed is reminiscent of smoke or lit gunpowder.

11. A computer program product for automatically dispensing a scent into an environment, the computer program product comprising:

one or more non-transitory computer readable storage media, and program instructions collectively stored on the one or more computer readable storage media, the program instructions comprising:

continuously detecting by a sensor or a computer processor, an audio signal in the environment;

forwarding data points in the audio signal to an artificial intelligence engine;

identifying, by the artificial intelligence engine, one or more precursors and patterns from the audio signal, associated with an event;

predicting by the artificial intelligence engine, an occurrence of the event based on the precursors and patterns identified in the audio signal;

forwarding the prediction to a computing device or a controller communicatively coupled to a scent dispenser;

identifying, by the computing device, a scent correlated to the event;

operating by the computing device or the controller, a dispense of the identified scent by the scent dispenser into the environment in association with a predicted occurrence of the event and determining by the computing device or controller, whether a frequency of dispense of the identified scent exceeds a threshold value within a window of time.

12. The computer program product of claim 11, wherein the audio signal is an analog signal.

13. The computer program product of claim 12, the analog sound is received from a speaker playing a sound track from a playback of an audio/visual media.

14. The computer program product of claim 11, wherein the audio signal is a digital audio stream.

15. The computer program product of claim 14, wherein the digital audio stream is received from one of a gaming console, a virtual reality system, a smart phone, a smart television or display, and a personal computer.

16. The computer program product of claim 11, wherein the program instructions further comprise preventing the scent dispenser from dispensing the scent in the event the threshold value is exceeded.

17. The computer program product of claim 11, wherein the scent is selected based on a smell reminiscent of the event.

18. The computer program product of claim 11, wherein the identified event occurs multiple times in the audio signal.

19. The computer program product of claim 11, wherein the predicted event occurs at an arbitrary point in the audio signal.

20. The computer program product of claim 11, wherein the predicted event is a gun fire or explosion and the scent dispensed is reminiscent of smoke or lit gunpowder.

* * * * *